United States Patent
Ahluwalia et al.

(10) Patent No.: US 8,010,179 B2
(45) Date of Patent: Aug. 30, 2011

(54) METHOD AND APPARATUS OF GRADIENT ECHO IMAGING WITH ON-THE-FLY OPTIMIZATION OF TISSUE SUPPRESSION

(75) Inventors: Baldev S. Ahluwalia, Milwaukee, WI (US); Cynthia F. Maier, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 2373 days.

(21) Appl. No.: 10/605,365

(22) Filed: Sep. 25, 2003

(65) Prior Publication Data
US 2005/0070785 A1  Mar. 31, 2005

(51) Int. Cl.
*A61B 5/05* (2006.01)
(52) U.S. Cl. ....................................... 600/410
(58) Field of Classification Search .................. 600/410; 324/306, 307–322
See application file for complete search history.

(56) References Cited

U.S. PATENT DOCUMENTS

| | | | | |
|---|---|---|---|---|
| 5,233,301 A * | 8/1993 | Meyer et al. | .................. | 324/309 |
| 5,256,967 A * | 10/1993 | Foo et al. | .................... | 324/311 |
| 5,422,572 A * | 6/1995 | Yao | .................... | 324/309 |
| 5,429,134 A * | 7/1995 | Foo | .................... | 600/413 |
| 6,320,377 B1 * | 11/2001 | Miyazaki et al. | ............ | 324/306 |
| 6,380,736 B1 * | 4/2002 | Hajnal | .................... | 324/306 |
| 6,498,946 B1 * | 12/2002 | Foo et al. | .................... | 600/410 |
| 6,526,307 B2 * | 2/2003 | Foo | .................... | 600/413 |
| 7,251,520 B2 * | 7/2007 | Shankaranarayanan et al. | .................... | 600/415 |
| 2006/0164082 A1* | 7/2006 | Foxall et al. | ................. | 324/306 |

* cited by examiner

*Primary Examiner* — Jacqueline Cheng
(74) *Attorney, Agent, or Firm* — Ziolkowski Patent Solutions Group, SC (57) ABSTRACT

The present invention provides a system and method for on-the-fly optimization of the timing of suppression pulses and a k-space filling scheme for user-prescribed imaging parameters. The invention also minimizes total data acquisition time for the sequence tailored to the particular user-prescribed imaging parameters. A pulse sequence uses a 180° pulse to invert the magnetization corresponding to the suppressed tissue so that a maximum amount of time is provided to play out alpha or imaging pulses after each inversion. The pulse sequence optimizes the number of alpha pulses played out after each inversion pulse based on a specific protocol or imaging parameters selected by the user. This pulse sequence allows for a modified k-space filling scheme that places, at the center of k-space, the echo that most closely corresponds to the null point of the suppressed tissue. For the first inversion pulse, a flip angle less than 180° is used to drive the suppressed tissue magnetization into a steady-state condition immediately.

19 Claims, 5 Drawing Sheets

METHOD AND APPARATUS OF GRADIENT ECHO IMAGING WITH ON-THE-FLY OPTIMIZATION OF TISSUE SUPPRESSION

BACKGROUND OF INVENTION

The present invention relates generally to MR imaging and, more particularly, to a method and apparatus of gradient echo imaging with on-the-fly optimization of tissue suppression.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals is digitized and processed to reconstruct the image using one of many well known reconstruction techniques.

To enhance a radiologist or other medical provider's ability to efficiently and effectively diagnose a particular pathology or abnormality, it is often desirable to suppress signal from certain tissues while simultaneously obtaining signal from other tissues. A number of data acquisition schemes have been developed for suppressing specific tissues. This method of tissue suppression can also eliminate signal based not only on frequency selection, but $T_1$. For example, one tissue suppression imaging technique implements a frequency selective saturation pulse that is applied before standard imaging pulses of a sequence. As a result, the saturation pulse sets to zero the magnetization of the particular tissue to be suppressed, e.g. fat. As such, when the standard imaging sequence is applied, no signal from the suppressed component or tissue is detected. Accordingly, the non-detected components will appear black on a reconstructed image and thereby provide contrast to the detected and imaged components or tissue. The tissue suppression techniques may be implemented with spin echo imaging as well as gradient echo imaging. For gradient echo imaging sequences, which are designed for rapid imaging, use of standard tissue suppression techniques dramatically increases acquisition time. This negatively affects patient throughput and increases the likelihood of patient movement during the imaging process which negatively affects the reconstructed image.

One proposed solution is to acquire several lines of k-space following each application of the tissue suppression technique. For this approach to be successful, the signal from the suppressed tissue must remain null for some time after the suppression technique is applied. The time and duration for which the suppressed tissue remains null after the saturation pulse varies with tissue $T_1$ and imaging parameters, i.e. resolution, receiver bandwidth, flip angle, TR, and the like. Despite the dependence of suppression time upon imaging parameters, known imaging techniques maintain a timing of the suppression pulses and k-space filling scheme regardless of the particular imaging parameters. This results in an unpredictable quality of tissue suppression and image artifacts.

It would therefore be desirable to have a system and method capable of setting, on-the-fly, timing of a series of suppression pulses as well as a k-space filling scheme that is optimized to fit particular user-prescribed imaging parameters for an imminent scan.

BRIEF DESCRIPTION OF INVENTION

The present invention provides a system and method for on-the-fly optimization of the timing of suppression pulses and a k-space filling scheme for user-prescribed imaging parameters that overcome the aforementioned drawbacks.

The invention minimizes total data acquisition time for the sequence tailored to the particular user-prescribed imaging parameters. In this regard, the present invention also includes a pulse sequence that uses a 180° pulse to invert the magnetization corresponding to the suppressed tissue so that a maximum amount of time is provided to play out alpha or imaging pulses after each inversion. The pulse sequence optimizes the number of alpha RF excitation pulses played out after each inversion pulse based on a specific acquisition protocol or imaging parameters selected by the user. This pulse sequence allows for a modified k-space filling scheme that places, at the center of k-space, the echo that most closely corresponds to the null point of the suppressed tissue. Additionally, for the first inversion pulse of the sequence, a flip angle less than 180° is used to drive the suppressed tissue magnetization into a steady-state condition immediately, thereby obviating the need for playing out discarded acquisitions during an approach to steady-state. As such, tissue suppression for the specific user-selected protocol or imaging parameters is optimized as well as total acquisition time reduced. The present invention may be used with spectrally selective inversion pulses to preferentially suppress a tissue at one particular ordinate frequency, e.g., fat, or with spatially selective inversion pulses to preferentially suppress tissue in a region affected by the pulses, e.g., a "saturation band", as well as any blood flowing through the targeted region at the time of the pulses. In addition, due to the tissue $T_1$ dependence on k-space filling order, this invention can also be used to suppress signal from tissues based on their longitudinal relaxation times.

Therefore, in accordance with one aspect of the present invention, a method of tissue suppression during gradient echo imaging includes the steps of identifying a set of user-selected imaging parameters for a prescribed MR data acquisition of a targeted tissue and setting the length of a train of tissue suppression pulses of a tissue suppression pulse sequence specific to the user-selected imaging parameters. The method further includes the step of applying the tissue suppression pulse sequence to selectively suppress data acquisition from the targeted tissue.

In accordance with another aspect of the invention, an MRI apparatus to acquire gradient echo data is disclosed. The apparatus includes an MRI system having a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MRI apparatus also includes a computer programmed to determine a null point of tissue targeted for suppression. The computer is further programmed to determine a time interval for longitudinal magnetization of the tissue to recover to the null point. From this time interval, the computer is programmed to determine a number of alpha pulses to be applied after each inversion pulse of a gradient echo pulse sequence.

According to another aspect of the present invention, a pulse sequence for gradient echo acquisition includes a first TR period and at least a second TR period. The pulse sequence includes a first inversion pulse having a flip angle less than 180° played out during the first TR period and a second inversion pulse having a flip angle of 180° played out in each subsequent TR. The pulse sequence further includes a number of RF alpha pulses played out during each TR period wherein a portion of the RF pulses is played out prior to zeroing of longitudinal magnetization of a tissue targeted for evaluation.

In accordance with another aspect of the invention, the invention is embodied in a computer program stored on a computer readable storage medium and having instructions which, when executed by a computer, cause the computer to identify a set of user-selected imaging parameters for an imminent MR scan of a targeted tissue. The instructions further cause the computer to determine, on-the-fly, a flip angle of a spectrally selective inversion pulse to be applied to immediately drive suppressed magnetization of the targeted tissue to steady-state as well as determine, on-the-fly, the number of suppression pulses to be applied after the spectrally selective inversion pulse such that suppression pulses are applied before and after the longitudinal magnetization of the target tissue reaches zero.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

A system is shown to optimize, on-the-fly, a gradient echo pulse sequence for tissue suppression. The system is designed to implement 2D and 3D gradient echo acquisitions.

Figure 1:
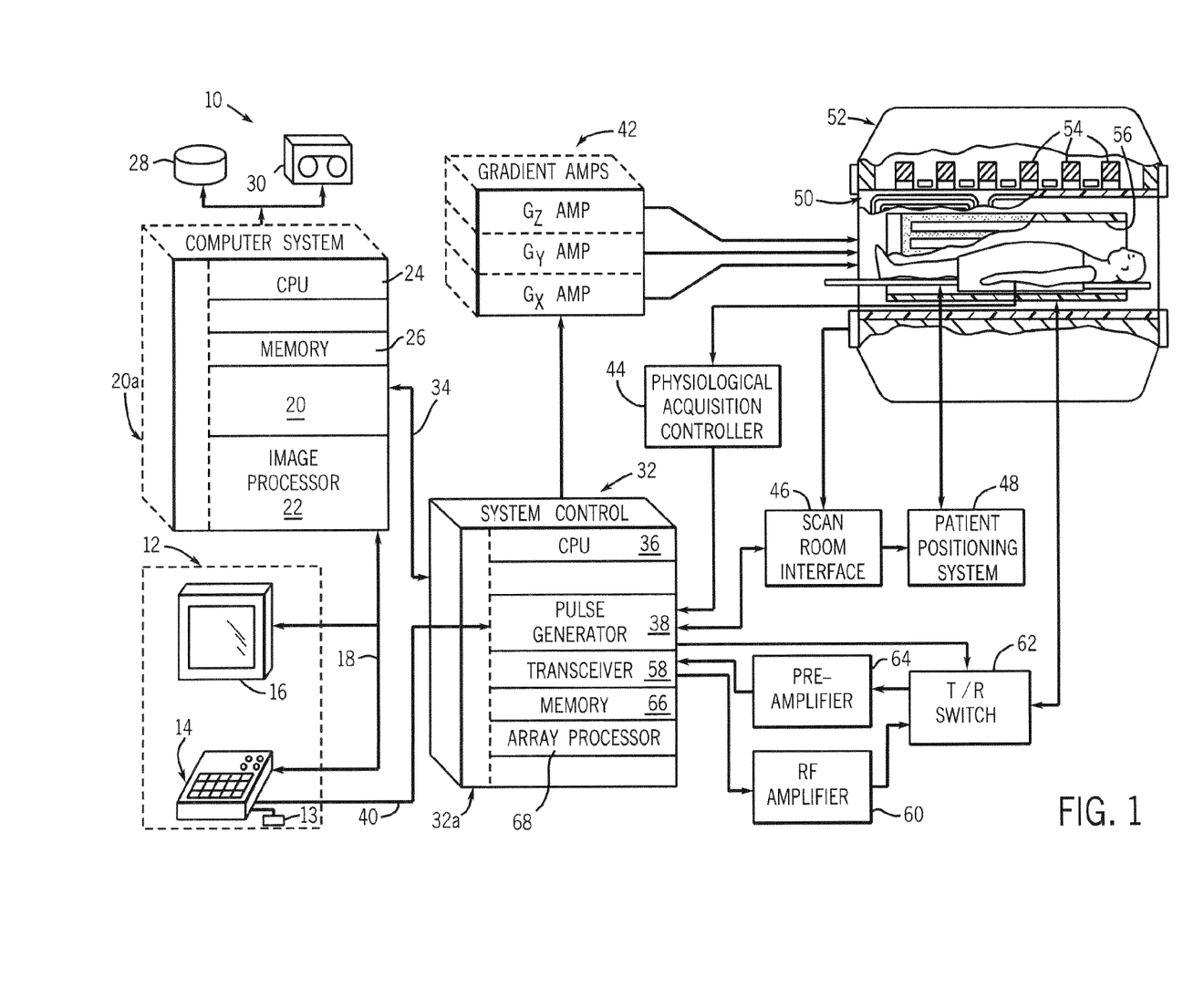
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. One skilled in the art will appreciate that other RF coils other than a whole body coil may be implemented. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention is directed to a pulse sequence that applies an optimal number of excitation RF pulses (alpha pulses) after an inversion pulse specific to imaging parameters identified by a user when prescribing the scan. The disclosed pulse sequence and optimization technique may be used to provide robust fat suppression for a number of user-prescribed imaging parameters. This eliminates image artifacts typically associated with fat suppression imaging techniques that acquire multiple lines of k-space after each application of a suppression pulse. The present invention is particularly well suited for fat suppressed imaging where it is necessary to use low alpha pulse flip angles in order to visualize areas of non-contrast enhanced tissue as well as areas of accumulated contrast agent. For example, the present invention is particularly suited for imaging breast, knee, and liver regions of a patient. Additionally, the present invention has been shown to improve tissue suppression in saturation bands for gradient echo sequences. In one empirical study, tissue suppression in a saturation band was increased from 49% to 91%. This invention can also be used to suppress tissue by its longitudinal relaxation constant. One such example is CSF signal suppression.

Figure 2:
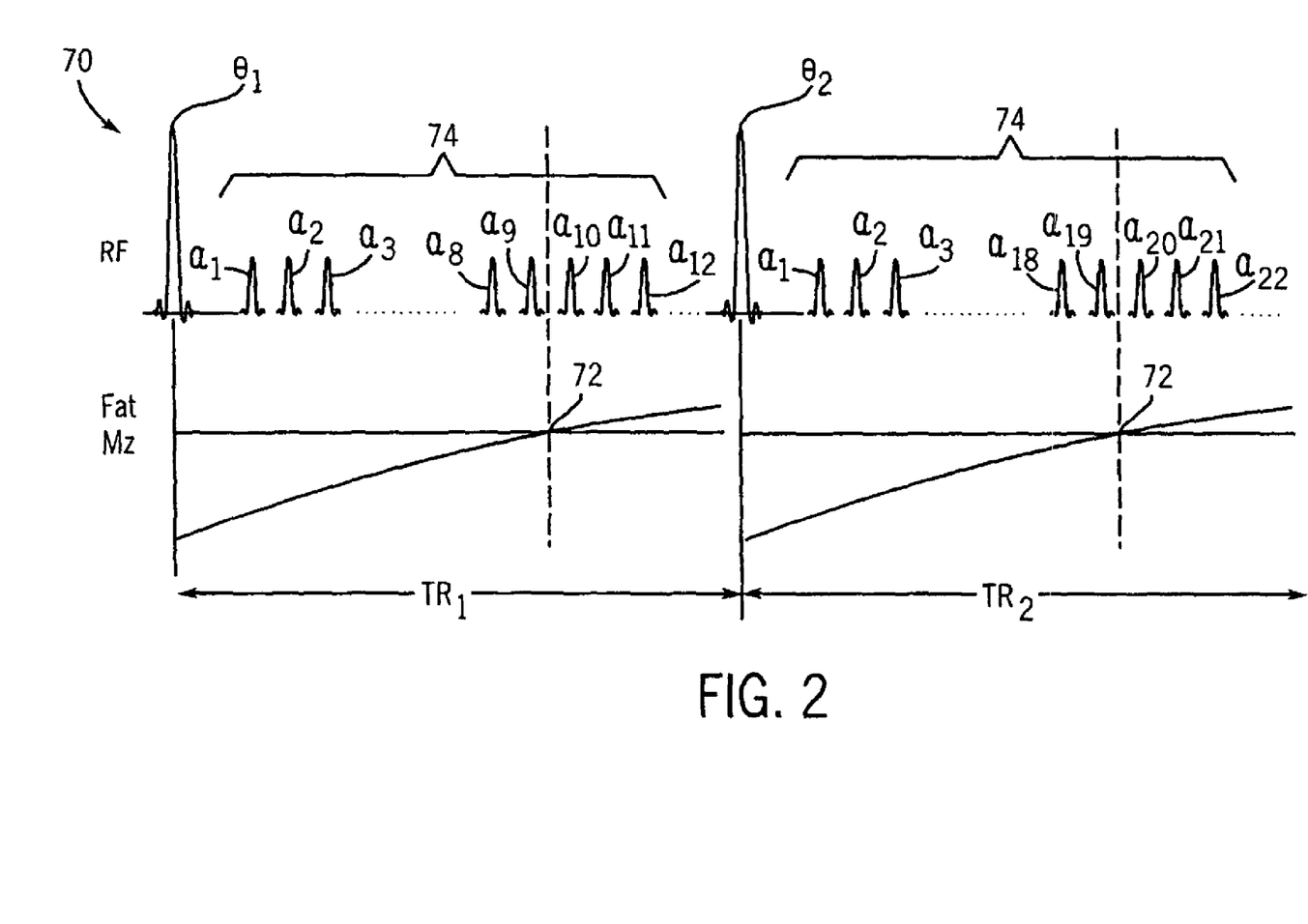
FIG. 2 is a graphical representation of a portion of a gradient echo pulse sequence in accordance with one embodiment of the present invention. .

Referring now to FIG. 2, a pulse sequence 70 in accordance with one aspect of the present invention is carried out over multiple TR cycles. Each TR cycle defines a period of data acquisition, i.e. time between alpha pulses. Pulse sequence 70 is defined by an inversion pulse θ that is applied at the beginning of each TR period. In pulse sequence 70, however, the spectrally selective inversion of pulses applied during the first TR period, $TR_1$, is different than the spectrally selective inversion pulse applied during each subsequent TR period, i.e. $TR_2$, $TR_3$, $TR_N$. Specifically, the spectrally selective inversion pulse $θ_1$ for $TR_1$ has a flip angle less than 180° whereas the spectrally selective inversion pulse, $θ_2$, for $TR_2$ and each subsequent TR has a flip angle of 180°. By using a flip angle of less than 180° for the first spectrally selective inversion pulse, the suppressed tissue magnetization is immediately driven to a steady-state condition thereby obviating the need for playing out discarded acquisitions during an approach to steady-state. That is, typically, the data acquired during the approach to steady-state is discarded and not used during image reconstruction. By immediately driving the suppressed magnetization into a steady-state condition, the total acquisition time is reduced.

For each TR thereafter, the spectrally selective inversion pulse has a flip angle of 180°. The 180° pulse inverts the magnetization corresponding to the suppressed tissue thereby maximizing the amount of time provided to play out alpha pulses after each inversion pulse. That is, using a 180° flip angle for the inversion pulse results in a longer delay between the inversion pulse and the null point 72 of the suppressed magnetization compared to the delay time associated with smaller inversion flip angles.

Still referring to FIG. 2, after each spectrally selective inversion pulse, a train of alpha pulses 74 is applied. The train of alpha pulses 74 allows multiple lines of k-space to be filled during a single TR. Since the number of pulses on each train 74 is optimized to provide the most effective tissue suppression, an optimal number of k-space lines to be acquired during each TR is used.

Additionally, as noted above, the train of alpha pulses 74 is applied immediately after the spectrally selective inversion pulse. As such, it is no longer required for a user to enter a TI interval for the pulse sequence. One skilled in the art will readily recognize the TI typically corresponds to the amount of time before data acquisition commences after an inversion pulse is applied. With TI dependent pulse sequences, data acquisition typically does not occur until after expiration of the TI period. However, with the present invention, data acquisition occurs immediately after the inversion pulse is applied rather than waiting for expiration of a delay period, i.e. TI. Further, the present invention also includes a modified k-space filling scheme that places at the center of k-space data from the echo that most closely corresponds to the null point of the suppressed tissue. The center of k-space is filled with data corresponding to a line when longitudinal magnetization from the suppressed tissue at or near zero.

Still referring to FIG. 2, the number of pulses of each train 74 depends upon particular imaging parameters for the scan as input by a user. As will be described in greater detail below, inputs relating to TR, receiver bandwidth, x-resolution, $T_1$ of the suppressed tissue, and alpha pulse flip angles are used to determine the optimal or maximum number of alpha pulses to apply after each inversion pulse.

Figure 3:
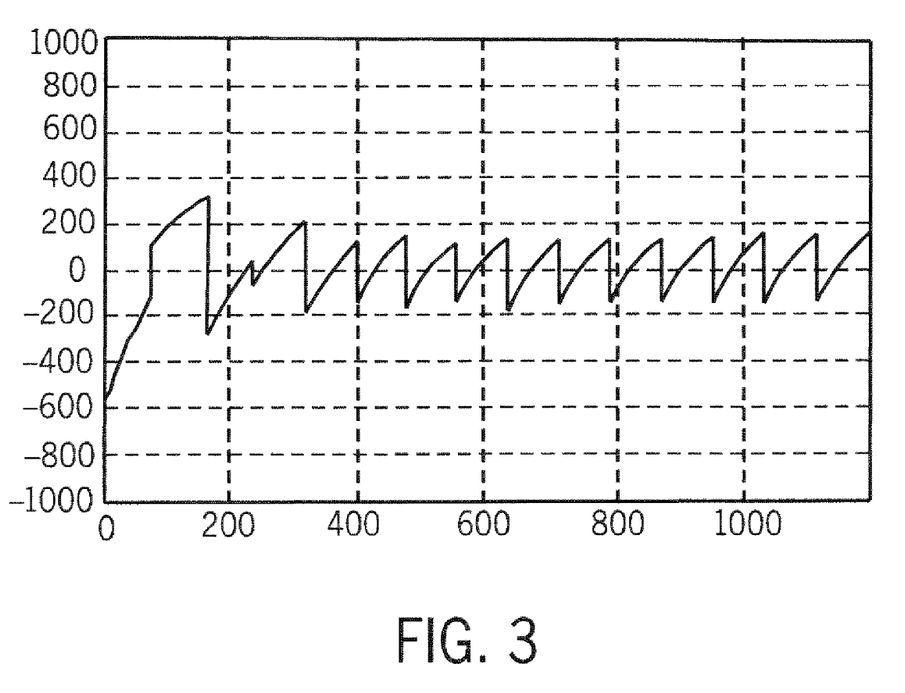
FIGS. 3-5 are graphs illustrating longitudinal magnetization from fat for three exemplary alpha pulse train lengths.
Figure 4:
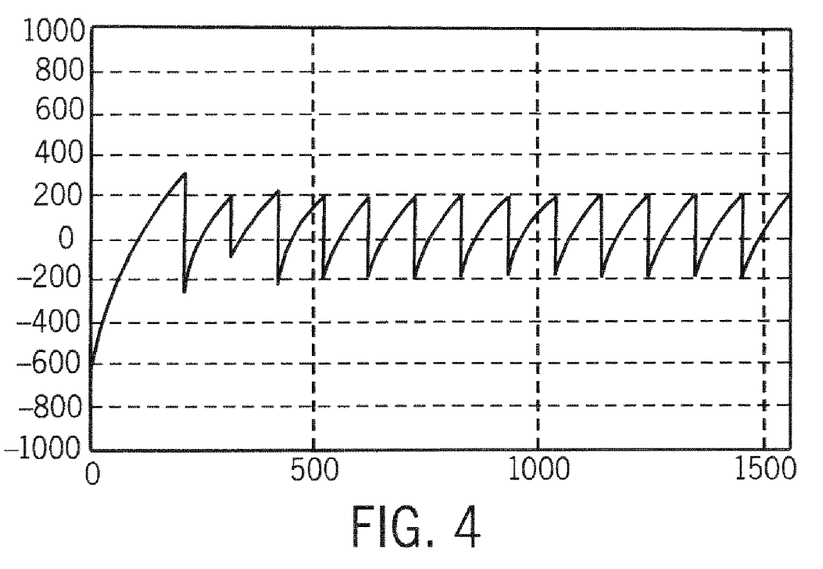
Figure 5:
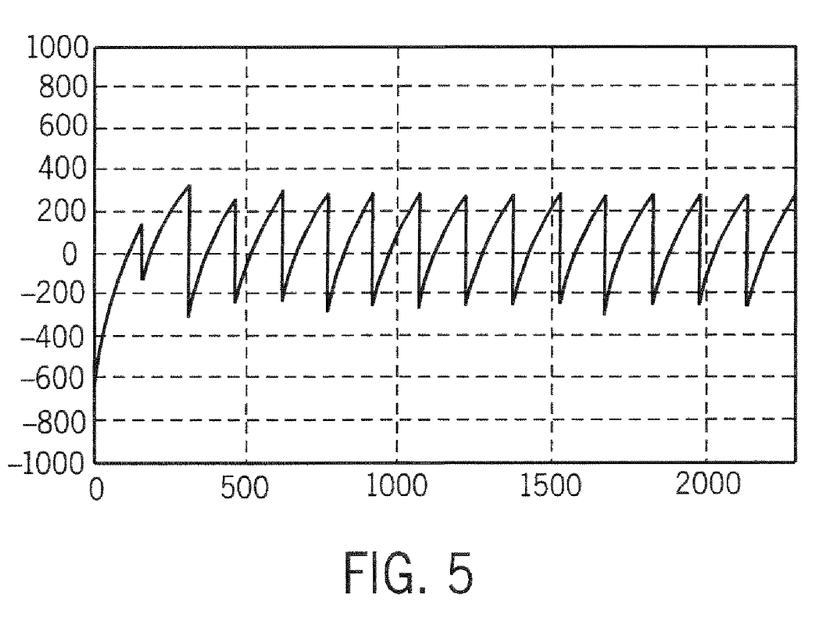

It has been discovered that longer alpha pulse trains result in greater recovery of the magnetization from fat, but also result in shorter acquisition times. For example, the magnetization recovery from fat for twelve alpha pulses has been found, in one example, to be significantly less than the initial value of magnetiZation, as shown in FIG. 3. Further, a train pulse having sixteen alpha pulses also results in a longitudinal magnetization recovery significantly less than the initial value of magnetization, as shown in FIG. 4. However, the amount of recovery with sixteen alpha pulses has been shown to be greater than the amount of recovery for a twelve pulse alpha pulse train. It is clear that a twenty-four pulse alpha pulse train results in substantially more recovery than that achieved with either a twelve or sixteen pulse alpha pulse train, as shown in FIG. 5. As noted above, an increasing number of alpha pulses in the pulse train also shortens the acquisition times of the entire data set, as fewer inversion pulses are necessary. The demand for patient throughput, and constraints of undesirable patient motion however, mandate minimum data acquisition time. As such, the user or pulse sequence developer is allowed to select or establish an upper threshold for magnetization recovery for the suppressed tissue. As such, the maximum number of pulses of the alpha pulse train that can be applied while suppressing the desired tissue below the user-selected threshold is used as the optimal number of pulses to apply.

Figure 6:
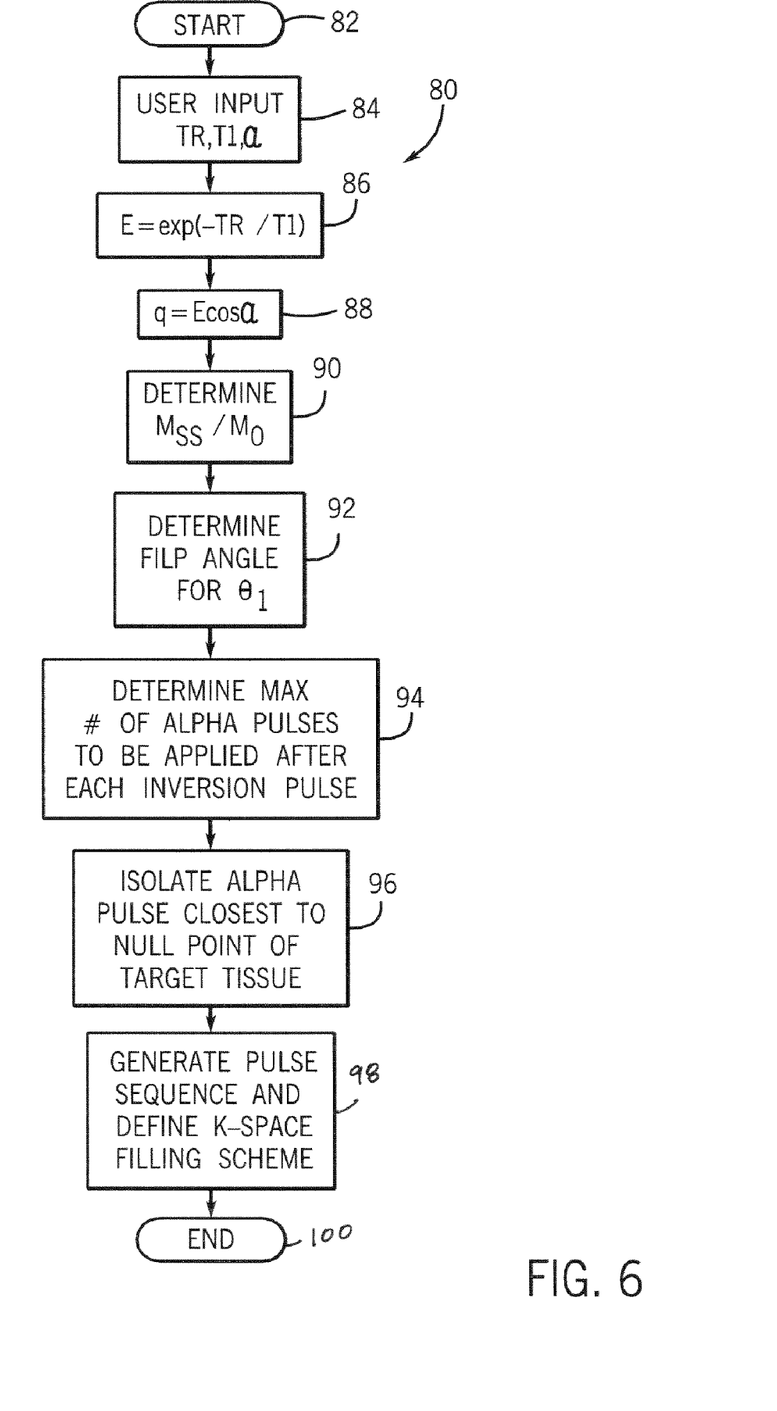
FIG. 6 is a flow chart setting forth the steps of on-the-fly optimization of tissue suppression in accordance with one embodiment of the present invention.

Referring now to FIG. 6, the acts/steps of a control algorithm for determining the optimum number of alpha pulses to be applied after each inversion pulse of a gradient echo pulse sequence are set forth. The acts/steps are preferably carried out "on-the-fly" such that the gradient echo pulse sequence is designed specifically and uniquely for imaging parameters of an imminent MR study. As will be described, a computer is configured to receive a series of user inputs identifying parameters of scan and from those specific inputs, develop an imaging sequence. The technique 80 begins at 82 with a user or pulse sequence developer inputting a series of imaging parameters for an imminent scan at 84. The user inputs may include receiver bandwidth (kHz), x-resolution, number of slices, y-resolution, TR, and the flip angle for each alpha pulse. From these user inputs, the algorithm determines a series of values that are used to calculate the optimum number of alpha pulses to be played out after each spectrally selective inversion pulse. For example, at step 86, the algorithm solves the following equation:

$$E = \exp(-T_R/T_1) \tag{Eqn. 1}$$

From this calculation, the algorithm solves the following equation at step 88:

$$q = E \cos(\alpha) \tag{Eqn. 2}$$

where "E" represents the value determined at step 86 and $\alpha$ corresponds to the flip angle of each alpha pulse.

From the value determined at step 88, the algorithm 80 determines at step 90 the ratio of steady-state magnetization of the tissue to be suppressed to the thermal equilibrium magnetization of the tissue to be suppressed in accordance with the following equation:

$$Mss = Mo[(1-\exp(-TI/T1))q^n + (1-E)(1-q^n)/(1-q)]/(1-\cos(\theta)\exp(-TI/T1)q^n) \tag{Eqn. 3}$$

where Mss is the longitudinal magnetization of the tissue to be suppressed, Mo is the thermal equilibrium magnetization of the tissue to be suppressed, T1 corresponds to the spin spin relaxation time of the tissue to be suppressed, TI is the default time following the inversion pulse before a first alpha pulse is applied, and n is a number of alpha pulses following each inversion pulse. As previously described, by setting an upper threshold for the maximum value of the ratio of $Mss/M_o$, suppression relative to $M_o$ may be determined. Using the calculated steady-state magnetization, the algorithm 80 can then determine the flip angle for the first inversion pulse at step 92. As set forth in the following equation, the flip angle for the first inversion pulse, $\theta_1$, is the arccosine of the ratio of steady-state magnetization to thermal equilibrium magnetization of the tissue to be suppressed. The corresponding equation follows:

$$\theta_1 = a\cos(Mss/Mo), \tag{Eqn. 4}$$

In determining the number of alpha pulses to be applied after each inversion pulse of each subsequent TR, a flip angle, $\theta$, of 180° is used. At step 94, algorithm 80 determines the maximum number of alpha pulses to be applied after each inversion pulse by solving Eqn. 3. After determining the number of alpha pulses to apply after each inversion pulse at step 94, the algorithm determines and isolates the alpha pulse closest to the null point of the target tissue at step 96. The null point coincides with the target tissue's longitudinal magnetization crossing zero on its way to recovery from inversion to its initial positive magnetization state. As such, filling the center of k-space with data from the echo corresponding to the null point of the target tissue would result in zero signal being detected from the suppressed tissue at that time. As such, if the target tissue is fat, the data corresponding to the center of k-space would not contain any data associated with a fat generated signal. Therefore, delineation between fat and water regions in the reconstructed image is improved. Once the alpha pulse closest to the null point of the target tissue is isolated, the algorithm 80 generates a pulse sequence and defines a k-space filling scheme at 98 particular to the imaging parameters identified by the user or pulse sequence generator at step 84 whereupon pulse sequence development for the particular imaging scan is complete and is implemented at step 100 to acquire data of a patient. As such, the pulse sequence in the k-space filling scheme is unique to the particular scan and is optimized for the particular scan.

The heretofore described algorithm results in improved tissue suppression, particularly for low flip angles. It should be noted, however, that the present invention is also robust for gradient echo sequences utilizing larger flip angles. A 180° spectrally selective inversion pulse to invert tissue magnetization so that the maximum amount of time is provided to play out alpha pulses after each inversion is disclosed. A modified k-space filling scheme that places at the center of k-space, data from the echo that most closely corresponds to the null point of the suppressed tissue is implemented. It should be noted, however, that for the first inversion pulse, a flip angle less than 180° is used in order to drive the suppressed tissue magnetization into a steady-state condition relatively immediately, thereby obviating the need for playing out discarded acquisitions during an approach to steady-state. Accordingly, the present invention optimizes tissue or fat suppression for the specific protocol being used to acquire data as well as reduces total acquisition time.

The present invention also contemplates implementation of dummy alpha pulses where no data is acquired to maintain an equilibrium if the modulus of a number of k-space lines to be acquired divided by the number of alpha pulses per TR is non-zero. Because the number of alpha pulses does not necessarily divide evenly into the number of k-space lines required to fill a k-space, the number of alpha pulses determined at step 94 of FIG. 6 may not provide a true optimal number of alpha pulses from the point of view of minimizing total acquisition time. That is, in many cases, the acquisition time may be decreased substantially by using a slightly lower value or number of alpha pulses than determined by algorithm 80, FIG. 6. As such, to calculate an ideal number of alpha pulses for these cases, a lower threshold for recovered magnetization may also be set by the user or pulse sequence developer. As such, from within this allowable range for steady-state magnetization, an optimal value of alpha pulses may be determined that minimizes the number of dummy alpha pulses that must be played out thereby minimizing the total acquisition time in those cases where dummy pulses are required.

Therefore, in accordance with one embodiment of the present invention, a method of tissue suppression during gradient echo imaging includes the steps of identifying a set of user-selected imaging parameters for a prescribed MR data acquisition of a targeted tissue and setting the length of a train of tissue suppression pulses of a tissue suppression pulse sequence specific to the user-selected imaging parameters. The method further includes the step of applying the tissue suppression pulse sequence to selectively suppress data acquisition from the targeted tissue.

In accordance with another embodiment of the invention, an MRI apparatus to acquire gradient echo data is disclosed. The apparatus includes an MRI system having a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MRI apparatus also includes a computer programmed to determine a null point of tissue targeted for suppression. The computer is further programmed to determine a time interval for longitudinal magnetization of the tissue to recover to the null point. From this time interval, the computer is programmed to determine a number of alpha pulses to be applied after each inversion pulse of a gradient echo pulse sequence.

According to another embodiment of the present invention, a pulse sequence for gradient echo acquisition includes a first TR period and at least a second TR period. The pulse sequence includes a first inversion pulse having a flip angle less than 180° played out during the first TR period and a second inversion pulse having a flip angle of 180° played out in each subsequent TR. The pulse sequence further includes a number of RF alpha pulses played out during each TR period wherein a portion of the RF pulses is played out prior to zeroing of longitudinal magnetization of a tissue targeted for evaluation.

In accordance with another embodiment of the invention, the invention is embodied in a computer program stored on a computer readable storage medium and having instructions which, when executed by a computer, cause the computer to identify a set of user-selected imaging parameters for an imminent MR scan of a targeted tissue. The instructions further cause the computer to determine, on-the-fly, a flip angle of a spectrally selective inversion pulse to be applied to immediately drive suppressed magnetization of the targeted tissue to steady-state as well as determine, on-the-fly, the number of suppression pulses to be applied after the spectrally selective inversion pulse such that suppression pulses are applied before and after the longitudinal magnetization of the target tissue reaches zero.

The present invention has been described in terms of the preferred embodiment, and it is recognized that equivalents, alternatives, and modifications, aside from those expressly stated, are possible and within the scope of the appending claims.

What is claimed is:

1. A method of tissue suppression during gradient echo imaging in an MRI apparatus comprising the steps of:
    identifying a set of user-selected imaging parameters for a prescribed MR data acquisition of a targeted tissue;
    setting a length of a train of alpha pulses of a gradient echo sequence specific to the user-selected imaging parameters, wherein the step of setting the length of a train of alpha pulses is carried out on-the-fly; and
    applying the gradient echo sequence to selectively acquire data from the targeted tissue in the MRI apparatus.

2. A method of tissue suppression during gradient echo imaging in an MRI apparatus comprising the steps of:
    identifying a set of user-selected imaging parameters for a prescribed MR data acquisition of a targeted tissue;
    setting a length of a train of alpha pulses of a gradient echo sequence specific to the user-selected imaging parameters, wherein the step of setting the length of a train of alpha pulses includes the step of determining an optimal number of RF pulses to be carried out after a spectrally selective inversion pulse; and
    applying the gradient echo sequence to selectively acquire data from the targeted tissue in the MRI apparatus.

3. The method of claim 2 wherein the spectrally selective inversion pulse is constructed to have a flip angle sufficient to drive longitudinal magnetization of the suppressed tissue into a steady state condition prior to application of a subsequent alpha pulse.

4. The method of claim 3 further comprising the step of applying another spectrally selective inversion pulse at TR, wherein the another spectrally selective inversion pulse has a flip angle of 180°.

5. The method of claim 2 wherein the step of applying includes applying the series of tissue suppression pulses immediately after the spectrally selective RF pulse.

6. A method of tissue suppression during gradient echo imaging in an MRI apparatus comprising the steps of:
    identifying a set of user-selected imaging parameters for a prescribed MR data acquisition of a targeted tissue;
    setting a length of a train of alpha pulses of a gradient echo sequence specific to the user-selected imaging parameters;
    applying the gradient echo sequence to selectively acquire data from the targeted tissue in the MRI apparatus; and
    placing, at a center of k-space, data corresponding to a gradient echo substantially corresponding to a null point of the suppressed tissue.

7. An MRI apparatus to acquire gradient echo data comprising:
    a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and
    a computer programmed to:
    (A) determine a null point of tissue to be suppressed;
    (B) determine a time interval for longitudinal magnetization of the tissue to recover to the null point; and
    (C) from the time interval, determine a number of alpha pulses to be applied after each inversion pulse of a gradient echo pulse sequence.

8. The MRI apparatus of claim 7 wherein the computer is further programmed to place at a center of k-space an echo substantially corresponding to the null point of the suppressed tissue.

9. The MRI apparatus of claim 7 wherein a first inversion pulse has a flip angle less than 180° and subsequent inversion pulses have a flip angle of 180°.

10. The MRI apparatus of claim 9 wherein the computer is further programmed to:
    determine an arccosine of a ratio between steady-state magnetization and thermal equilibrium magnetization; and
    set the flip angle of the first inversion pulse to the arccosine.

11. The MRI apparatus of claim 7 wherein the computer is further programmed to apply one of a 2D gradient echo acquisition and a 3D gradient echo acquisition.

12. The MRI apparatus of claim 7 wherein the computer is further programmed to carry out acts (A)-(C) on-the-fly.

13. The MRI apparatus of claim 12 wherein the computer is further programmed to identify a set of user inputs identifying receiver bandwidth, x-resolution, TR, $T_1$ of the tissue, flip angle, y-resolution, and number of slices.

14. A non-transitory computer readable storage medium having a computer program to implement a gradient echo acquisition and representing a set of instructions that when executed by a computer causes the computer to:
    apply a first inversion pulse having a flip angle less than 180° played out during a first TR period;
    apply a second inversion pulse having a flip angle of 180° played out during each subsequent TR period; and
    apply a number of RF alpha pulses played out during each TR period, wherein a portion of the alpha pulses is played out prior to zeroing of longitudinal magnetization of a tissue targeted for evaluation in the MRI apparatus, and wherein the number of RF alpha pulses played out during each TR period is modified based on the flip angle of the inversion pulse for each TR period.

15. The non-transitory computer readable storage medium of claim 14 wherein the flip angle of the first inversion pulse is set to a value sufficient to immediately drive suppressed transverse magnetization of the tissue to steady-state.

16. A non-transitory computer readable storage medium having a computer program to implement a gradient echo acquisition and representing a set of instructions that when executed by a computer causes the computer to:
    identify a set of user-selected imaging parameters for an imminent MR scan of a targeted tissue;
    on-the-fly, determine a flip angle of a spectrally selective inversion pulse to be applied to immediately drive suppressed magnetization of the targeted tissue to steady-state; and on-the-fly, determine a number of alpha pulses specific to the user-selected imaging parameters to be applied after the spectrally selective inversion pulse such that alpha pulses are applied before and after longitudinal magnetization of the targeted tissue reaches zero.

17. The non-transitory computer readable storage medium of claim 16 wherein the set of instructions further causes the computer to reset the flip angle of the spectrally selective inversion pulse to 180° after expiration of a first TR period.

18. The non-transitory computer readable storage medium of claim 16 wherein the set of instructions further causes the computer to fill k-space such that an echo substantially corresponding to a null point of the targeted tissue fills a center of k-space.

19. The non-transitory computer readable storage medium of claim 16, wherein the set of instructions further causes the computer to place, at a center of k-space, data corresponding to a gradient echo substantially corresponding to a null point of the suppressed tissue.

* * * * *